(12) United States Patent
Kittel et al.

(10) Patent No.: US 11,014,203 B2
(45) Date of Patent: May 25, 2021

(54) SYSTEM FOR APPLYING INTERFACE MATERIALS

(71) Applicant: Laird Technologies, Inc., Earth City, MO (US)

(72) Inventors: Mark D. Kittel, Berea, OH (US); Jason L. Strader, Cleveland, OH (US)

( * ) Notice: Subject to any disclaimer, the term of this patent is extended or adjusted under 35 U.S.C. 154(b) by 224 days.

(21) Appl. No.: 15/207,444

(22) Filed: Jul. 11, 2016

(65) Prior Publication Data

US 2018/0009072 A1    Jan. 11, 2018

(51) Int. Cl.
*H01L 21/67* (2006.01)
*H05K 7/20* (2006.01)
(Continued)

(52) U.S. Cl.
CPC .............. *B23P 15/26* (2013.01); *B29C 63/02* (2013.01); *H01L 21/4803* (2013.01); *H01L 21/4882* (2013.01); *H01L 21/67132* (2013.01); *H01L 23/42* (2013.01); *H01L 24/743* (2013.01); *H05K 7/2039* (2013.01); *B23K 20/18* (2013.01); *B29C 63/0013* (2013.01); *C07C 323/00* (2013.01); *C08L 53/02* (2013.01); *H01L 24/40* (2013.01); *H01L 24/95* (2013.01); *H01L 24/97* (2013.01);
(Continued)

(58) Field of Classification Search
CPC .. Y10T 156/107; Y10T 156/108; B23P 15/26; H01L 21/4803; H01L 21/4882; H01L 23/42; H01L 24/97; H01L 24/40; H01L 24/95; H01L 21/67132; H01L 27/14618; H01L 24/743; H01L 2224/27436; H01L 2224/32245; H01L 2224/83192; B29C 63/0013; B29C 63/02; C07C 323/00; C08L 53/02; B23K 20/18; H05K 7/2039
See application file for complete search history.

(56) References Cited

U.S. PATENT DOCUMENTS 3,707,762 A * 1/1973 Bochinski ............ H05K 3/3489
                                                        228/193
4,058,537 A * 11/1977 Mueller ................ C07C 323/00
                                                        549/242
(Continued)

FOREIGN PATENT DOCUMENTS

EP        2814057 A2    12/2014
JP      2002110890 A     4/2002
(Continued)

OTHER PUBLICATIONS

Machine Language Translation of Japanese Patent Publication JP 2005-327923, Nov. 2005. (Year: 2020).*
(Continued)

*Primary Examiner* — A. Dexter Tugbang
(74) *Attorney, Agent, or Firm* — Harness, Dickey & Pierce, P.L.C.; Anthony G. Fussner (57) ABSTRACT

A system for applying thermal interface materials to components includes a supply of thermal interface material and a die. The die is operable for pushing against and/or removing a portion of the thermal interface material that is between the die and a corresponding one of the components. The portion of the thermal interface material is removed from the supply and applied to the corresponding one of the components.

29 Claims, 3 Drawing Sheets

(51) Int. Cl.
*B23P 15/26* (2006.01)
*H01L 23/42* (2006.01)
*H01L 21/48* (2006.01)
*B29C 63/02* (2006.01)
*H01L 23/00* (2006.01)
*B29C 63/00* (2006.01)
*C07C 323/00* (2006.01)
*C08L 53/02* (2006.01)
*H01L 27/146* (2006.01)
*B23K 20/18* (2006.01)

(52) U.S. Cl.
CPC .............. *H01L 27/14618* (2013.01); *H01L 2224/27436* (2013.01); *H01L 2224/32245* (2013.01); *H01L 2224/83192* (2013.01); *Y10T 156/107* (2015.01); *Y10T 156/108* (2015.01)

(56) References Cited

U.S. PATENT DOCUMENTS

| | | | |
|---|---|---|---|
| 4,199,490 A * | 4/1980 | Kamiya | C08L 53/02 524/501 |
| 4,678,115 A * | 7/1987 | Weisert | B23K 20/18 156/210 |
| 4,732,631 A * | 3/1988 | Shimizu | Y10T 156/108 156/248 |
| 4,863,551 A * | 9/1989 | Ogura | Y10T 156/107 156/378 |
| 4,872,258 A | 10/1989 | Ragard | |
| 4,924,351 A * | 5/1990 | Kato | H01L 24/40 174/548 |
| 5,700,340 A * | 12/1997 | Johnson | Y10T 156/107 156/152 |
| 5,943,557 A * | 8/1999 | Moden | H01L 24/97 257/E23.039 |
| 6,391,686 B1 * | 5/2002 | Shiozawa | H01L 24/97 257/E21.514 |
| 6,987,671 B2 | 1/2006 | Houle | |
| 7,004,244 B2 | 2/2006 | Rauch | |
| 7,229,683 B2 | 6/2007 | Fischer et al. | |
| 7,229,852 B2 | 6/2007 | Hoshika | |
| 7,821,126 B2 | 10/2010 | Houle et al. | |
| 7,906,845 B1 | 3/2011 | Galloway et al. | |
| 8,119,427 B1 * | 2/2012 | Lu | H01L 24/95 257/E21.514 |
| 8,445,102 B2 | 5/2013 | Strader et al. | |
| 8,545,987 B2 | 10/2013 | Strader et al. | |
| 8,916,419 B2 | 12/2014 | Chen et al. | |
| 8,920,919 B2 | 12/2014 | Arora et al. | |
| 9,257,364 B2 | 2/2016 | Ahuja et al. | |
| 9,316,447 B2 | 4/2016 | Fleskens et al. | |
| 9,330,998 B2 | 5/2016 | Strader et al. | |
| 9,418,912 B2 | 8/2016 | Nardi et al. | |
| 9,472,485 B2 | 10/2016 | Saeidi et al. | |
| 10,741,519 B2 | 8/2020 | Strader et al. | |
| 2002/0050061 A1 | 5/2002 | Komyoji et al. | |
| 2003/0037866 A1 | 2/2003 | Aoki et al. | |
| 2004/0180474 A1 | 9/2004 | Oman | |
| 2004/0188814 A1 | 9/2004 | Houle et al. | |
| 2004/0261980 A1 | 12/2004 | Dani et al. | |
| 2004/0262372 A1 | 12/2004 | Houle et al. | |
| 2004/0262743 A1 | 12/2004 | Houle et al. | |
| 2005/0236107 A1 | 10/2005 | Doi | |
| 2005/0264677 A1 * | 12/2005 | Uchida | H01L 27/14618 348/340 |
| 2007/0193672 A1 | 8/2007 | Yamamoto | |
| 2009/0223638 A1 * | 9/2009 | Nonaka | H01L 21/67132 156/538 |
| 2009/0229732 A1 * | 9/2009 | Determan | H01L 21/67132 156/60 |
| 2009/0263938 A1 * | 10/2009 | Ino | H01L 24/97 438/124 |
| 2010/0252191 A1 * | 10/2010 | Nakata | H01L 21/67132 156/285 |
| 2011/0117706 A1 * | 5/2011 | Nishio | H01L 21/67132 438/127 |
| 2011/0135911 A1 * | 6/2011 | Maenaka | H01L 23/42 428/327 |
| 2014/0199790 A1 * | 7/2014 | Abe | H01L 24/97 438/7 |
| 2014/0367847 A1 | 12/2014 | Strader et al. | |
| 2016/0160104 A1 | 6/2016 | Bruzda et al. | |
| 2016/0185074 A1 | 6/2016 | Kagawa | |
| 2016/0315030 A1 | 10/2016 | Strader et al. | |
| 2016/0326419 A1 | 11/2016 | Balandin | |

FOREIGN PATENT DOCUMENTS

| | | |
|---|---|---|
| JP | 2005327923 A | 11/2005 |
| JP | 2009164322 A | 7/2009 |
| JP | 2012084688 A * | 4/2012 |
| KR | 10-0827725 B1 | 5/2008 |
| WO | WO-97/41599 A1 | 11/1997 |
| WO | WO-2016182996 A1 | 11/2016 |

OTHER PUBLICATIONS

European Search Report for EP17178138.8 filed Jun. 27, 2017 which claims priority to the instant application, dated Dec. 13, 2017, 6 pages.

Hirschi, David; Dow Corning Case Study; Understanding Differences Between Thermal Interface Materials: Improve your ability to specify the optimum TIM; Copyright 2008, 4 pages.

Types of Fabricated Films and Pad Thermal Interface Materials—Dow Corning; Thermal Interface—Wet Dispensed; http://www.dowcorning.com/content/etronics/etronicswet/newtim_tutorial5.asp; accessed Jul. 11, 2016.

Basics of Processing for Fabricated Films and Pads—Dow Corning; Thermal Interface—Wet Dispensed; hhttp://www.dowcorning.com/content/etronics/etronicswet/newtim_tutorial13.asp accessed Jul. 11, 2016; 1 page.

Packaging and Storage Considerations—Dow Corning; http://www.dowcorning.com/content/etfonics/etronicswet/newtim_tutorial14.asp accessed Jul. 11, 2016.

Korean Office Action dated Oct. 22, 2018 issued in Application No. 10-2017-0085269 which claims priority to this U.S. Appl. No. 15/207,444, 15 pages. An English language translation of the Korean Office Action is not available at this time.

Non-final Office Action for U.S. Appl. No. 16/114,687 which is a continuation-in-part of the instant application; dated Nov. 15, 2019, 12 pages.

Final Office Action for U.S. Appl. No. 16/114,687 which claims priority to the instant application; dated May 14, 2020, 13 pages.

* cited by examiner

SYSTEM FOR APPLYING INTERFACE MATERIALS

FIELD

The present disclosure relates to systems and methods of applying thermal interface materials (TIMs).

BACKGROUND

This section provides background information related to the present disclosure which is not necessarily prior art.

Electrical components, such as semiconductors, integrated circuit packages, transistors, etc., typically have pre-designed temperatures at which the electrical components optimally operate. Ideally, the pre-designed temperatures approximate the temperature of the surrounding air. But the operation of electrical components generates heat. If the heat is not removed, the electrical components may then operate at temperatures significantly higher than their normal or desirable operating temperature. Such excessive temperatures may adversely affect the operating characteristics of the electrical components and the operation of the associated device.

To avoid or at least reduce the adverse operating characteristics from the heat generation, the heat should be removed, for example, by conducting the heat from the operating electrical component to a heat sink. The heat sink may then be cooled by conventional convection and/or radiation techniques. During conduction, the heat may pass from the operating electrical component to the heat sink either by direct surface contact between the electrical component and heat sink and/or by contact of the electrical component and heat sink surfaces through an intermediate medium or thermal interface material. The thermal interface material may be used to fill the gap between thermal transfer surfaces, in order to increase thermal transfer efficiency as compared to having the gap filled with air, which is a relatively poor thermal conductor.

Heat spreaders are commonly used to spread the heat from one or more heat generating components such that the heat is not concentrated in a small area when transferred to a heat sink. An integrated heat spreader (IHS) is a type of heat spreader that may be used to spread the heat generated by operation of a central processing unit (CPU) or processor die. An integrated heat spreader or lid (e.g., a lid of an integrated circuit (IC) package, etc.) is typically a thermally-conductive metal (e.g., copper, etc.) plate that rests on top of the CPU or processor die.

Heat spreaders are also commonly used (e.g., as a lid, etc.) to protect chips or board-mounted electronic components often in conjunction with a sealed package. Accordingly, a heat spreader may also be referred to herein as a lid and vice versa.

A first thermal interface material or layer(s) (referred to as TIM1) may be used between an integrated heat spreader or lid and a heat source to reduce hot spots and generally reduce the temperature of the heat generating components or device. A second thermal interface material or layer(s) (referred to as TIM2) may be used between the lid or integrated heat spreader and the heat sink to increase thermal transfer efficiency from the heat spreader to the heat sink.

Figure 1:
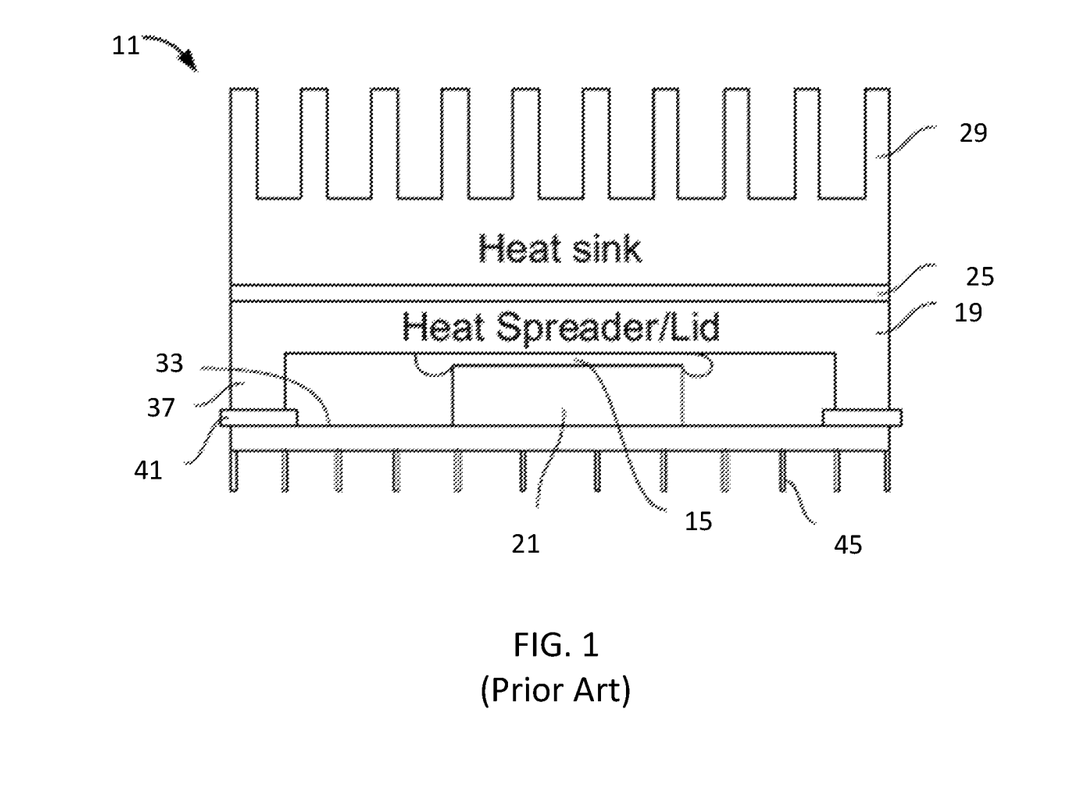
FIG. 1 is a cross-sectional view of an exemplary electronic device showing a thermal interface material (TIM1) positioned between a lid (e.g., integrated heat spreader (IHS), etc.) and a heat source (e.g., one or more heat generating components, central processing unit (CPU), die, semiconductor device, etc.)

For example, FIG. 1 illustrates an exemplary electronic device 11 having a TIM1 or first thermal interface material 15. As shown in FIG. 1, the TIM1 or thermal interface material 15 is positioned between a heat spreader or lid 19 and a heat source 21, which may comprise one or more heat generating components or devices (e.g., a CPU, die within underfill, semiconductor device, flip chip device, graphics processing unit (GPU), digital signal processor (DSP), multiprocessor system, integrated circuit, multi-core processor, etc.). A TIM2 or second thermal interface material 25 is positioned between a heat sink 29 and the heat spreader or lid 19.

By way of example, the heat source 21 may comprise a central processing unit (CPU) or processor die mounted on a printed circuit board (PCB) 33. The PCB 33 may be made of FR4 (flame retardant fiberglass reinforced epoxy laminates) or other suitable material. Also in this example, the heat spreader or lid 19 is an integrated heat spreader (IHS), which may comprise metal or other thermally-conductive structure. The heat spreader or lid 19 includes a perimeter ridge, flange, or sidewall portions 37. Adhesive 41 is applied to and along the perimeter ridge 37 for attaching the heat spreader or lid 19 to the PCB 33. The perimeter ridge 37 may thus protrude sufficiently downward to extend around the silicone die on the PCB 33 and thereby allow contact between the adhesive 41 on the perimeter ridge 37 and the PCB 33. Advantageously, adhesively attaching the heat spreader or lid 19 to the PCB 33 may also help stiffen the package, which is attached to the base PCB. Also shown in FIG. 1 are pin connectors 45. The heat sink 29 may generally include a base from which outwardly protrude a series of fins.

DRAWINGS

The drawings described herein are for illustrative purposes only of selected embodiments and not all possible implementations, and are not intended to limit the scope of the present disclosure.

DETAILED DESCRIPTION

Example embodiments will now be described more fully with reference to the accompanying drawings.

Conventional phase change material (PCM) application processes oftentimes include tabbed PCM parts and are relatively high in cost. There may be issues with the end users or customers applying the tabbed parts correctly and/or issues with the liner release. With conventional application processes, the part configurations, shape, and size of the TIM are limited. Also, it can be difficult to keep the PCM material clean during any additional steps after forming in a clean room. It can also be difficult to ship tabbed parts without distortion. After recognizing the above, the inventors hereof developed and disclose herein exemplary embodiments of systems and processes for applying (e.g., tamping and cutting, etc.) thermal interface materials (TIMs) to a wide range of substrates and components, such as lids or integrated heat spreaders of integrated circuit (IC) packages, board level shields (e.g., a removable lid or cover of a board level shield (BLS), etc.), heat sources (e.g., a central processing unit (CPU), etc.), heat removal/dissipation structures or components (e.g., a heat spreader, a heat sink, a heat pipe, a vapor chamber, a device exterior case or housing, etc.), etc.

Figure 3:
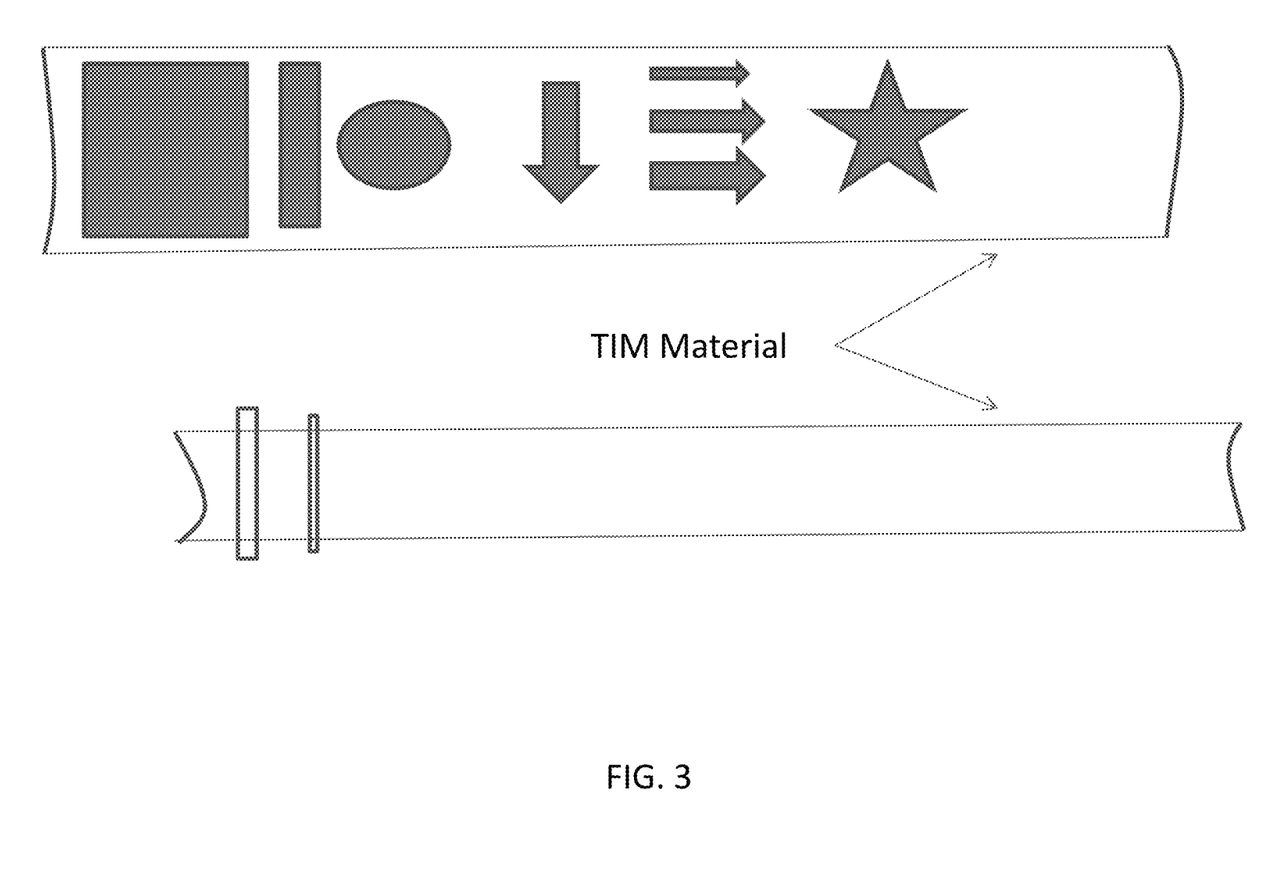
FIG. 3 illustrates exemplary die shapes (e.g., star, arrow, square, rectangular, oval, etc.) that are possible for the thermal interface materials using the system according to the exemplary embodiment shown in FIG. 2.

In exemplary embodiments disclosed herein, a die may be used that is tailored or customized (e.g., shaped and sized, etc.) according to a customer required size and shape (e.g., one or more of the shapes shown in FIG. 3, etc.). The die is pressed and moved downwardly through a liner (e.g., a polyethylene terephthalate (PET) carrier and/or release liner, etc.) that is disposed along a top or upper surface of a thermal interface material (e.g., phase change material (PCM), other TIM, etc.) with pressure, dwell, heating, and cooling. As the die is pressed and moves downwardly through the liner, the downward movement of the die also moves and applies the TIM downwardly onto a substrate or component, such as a lid or an integrated heat spreader of an integrated circuit (IC) package, a lid or cover of a board level shield (BLS), a heat source (e.g., a central processing unit (CPU), etc.), a heat removal/dissipation structure (e.g., a heat spreader, a heat sink, a heat pipe, a vapor chamber, a device exterior case or housing, etc.), etc. When the die is removed and raised upwardly away from the TIM, the liner is also removed from the TIM. The TIM in the specific customer required size and shape remains left behind, e.g., on the lid, BLS, heat source, heat removal/dissipation structure, etc. The machine or press used to press the die downwardly through the liner may range from a manual hand operated press to a highly automated machine.

In exemplary embodiments, the TIM comprises a phase change material (PCM) or other non-metal TIM (e.g., plastic TIM, silicone elastomer TIM, etc.). In exemplary embodiments, a center foam core is used to tamp the TIM down onto the substrate or component (e.g., lid, BLS, heat source, heat removal/dissipation structure, etc.) and then a die is used to the cut the TIM through the liner without having to puncture the liner to make the cut. In exemplary embodiments, the TIM is non-metal such that there is no diffusion bonding or welded joints between the non-metal TIM and the substrate or component (e.g., lid, BLS, heat source, heat removal/dissipation structure, etc.). Instead, the non-metal TIM may be naturally tacky and self-adhere to the substrate or component without any additional adhesive needed (although adhesives could also be used).

Figure 2:
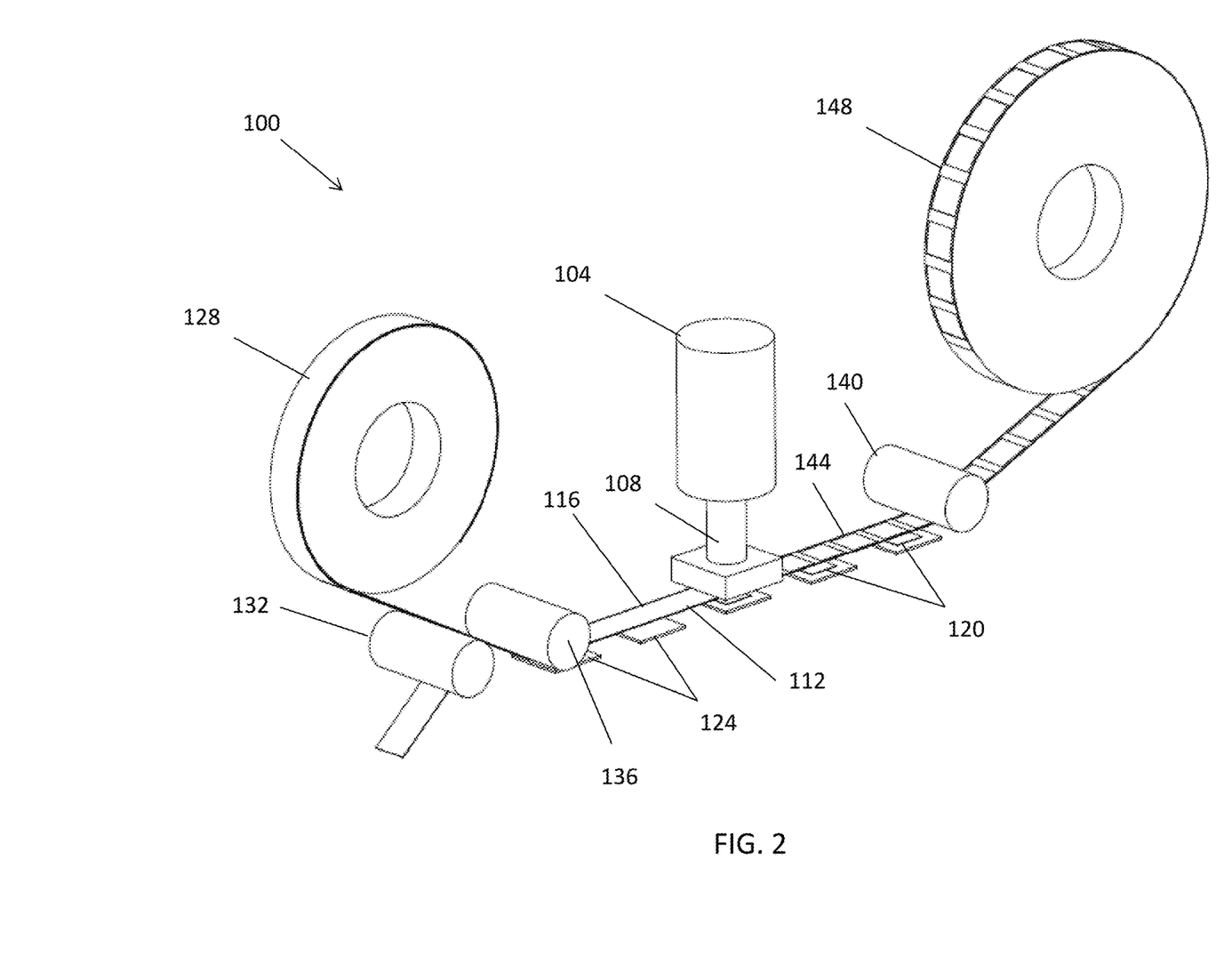
FIG. 2 illustrates an exemplary system for applying (e.g., tamping and cutting, etc.) thermal interface materials to lids according to an exemplary embodiment.

With reference to the figures, FIG. 2 illustrates an exemplary system 100 for applying (e.g., tamping and cutting, etc.) thermal interface materials to lids (e.g., integrated heat spreaders, etc.) according to an exemplary embodiment embodying one or more aspects of the present disclosure. Although FIG. 2 shows the thermal interface materials 120 being applied to lids 124, the system 100 may also be used for applying the thermal interface materials 120 to a wide range of other components and substrates, such as board level shields (e.g., a removable lid or cover of a board level shield (BLS), etc.), heat sources (e.g., a central processing unit (CPU), etc.), heat removal/dissipation structures or components (e.g., a heat spreader, a heat sink, a heat pipe, a vapor chamber, a device exterior case or housing, etc.), etc. Accordingly, aspects of the present disclosure should not be limited to use with any single type of substrate, part, or component or limited to application of thermal interface materials to any specific location or portion of the substrates, parts, or components.

As shown in FIG. 2, the system 100 includes a press 104 coupled with a die 108. In operation, the press 104 and die 108 are operable for tamping and cutting the portion of the strip 112 that includes a liner 116 and thermal interface material (TIM) 120 that is underneath the die 108.

By way of example, the die 108 may comprise a rounded knife die. The rounded knife die may include a foam filled core. In alternative embodiments, the die 108 may not require a foam core depending on the particular type of thermal interface material being applied.

In this example, the foam filled core may tamp the TIM 120 downward onto a corresponding one of the lids 124 located underneath the die 108. Then, the rounded knife die may be used to cut the TIM 120 through the liner 116, e.g., without having to puncture the liner 116 to make the cut, etc. During this cutting operation, the TIM 120 is squeezed down and the liner 116 is pushed through the TIM 120 with the die 108, which causes severing of the TIM 120 from itself but not cutting the liner 116. Although a very thin portion of the TIM 120 may be left between the lid 124 and the liner 116, the portion is so thin that it still breaks free from the rest of the TIM 120 essentially cutting the TIM 120. By way of example, the TIM 120 may start at an initial thickness of about 125 microns. The die 108 may force the liner 116 down into the TIM 120 until the TIM thickness is reduced to about 25 microns or is pushed out of the way. Accordingly, the TIM 120 may thus have tapered edges on all four sides due to this cutting method.

As shown in FIG. 2, the TIM 120 may remain on the lid 124 when the die 108 is removed and the next portion of the strip 112 and the next lid 124 is moved into place under the die 108. By way of example, the lids 124 may progress or move relative to the die 108 via a conveyor belt or other feeding/conveyor mechanism.

In this illustrated embodiment, the strip of material 112 that includes the liner 116 and TIM 120 is roll stock from a supply or roll 128. Rollers 132, 136, 140 are used to cause the strip of material 112 to unroll from the supply 128 of roll stock and travel to the location underneath the die 108 for tamping and cutting. After the TIMs 120 has been tamped, cut, and applied to the lids 124, what is left of the strip of material 144 is collected or wound onto the salvage roll 148. In other embodiments, more or less rollers may be used and/or strips of material that do not come on rolls may be used. In which case, the strips of material may be put in place by hand, with a jig, or by an automated means.

In an exemplary embodiment, the system 100 preferably uses as much of the strip of material as possible to thereby minimize or at least reduce waste (e.g., minimize the amount of TIM material left on the liner, etc.) during the application process. As shown in FIG. 2, the lids 124 are spaced apart by a greater distance than which the strip 112 is advanced after each tamping and cutting operation. After each tamping and cutting operation, the strip 112 is advanced only enough (e.g., a minimum distance, etc.) to allow the next portion of the strip 112 to be tamped and cut in order to apply the TIM 120 to the next lid 124. In an exemplary embodiment, the width of the TIM 120 along the liner 116 may be equal to the width of the pieces of the TIM 120 that are tamped, cut, and applied to the lids 124. In another exemplary embodiment, the width (e.g., 1 inch, etc.) of the TIM 120 along the liner 116 may be greater than the width (e.g., ¾ inches, etc.) of the pieces of the TIM 120 that is tamped, cut, and applied to the lids 124.

In exemplary embodiments, the strip of material 112 may also include a lower liner disposed along a lower surface or bottom of the TIM 120. In such embodiments, the lower liner may be manually removed by hand or automatically without manual intervention (e.g., with a rewind and stripper bar, etc.) before the die 108 applies the TIM 120 to the lids 124.

In exemplary embodiments, the system 100 may include one or more heaters such that heat is applied or added to the top and/or such that heat is applied or added to the base or bottom. Additionally, or alternatively, the system 100 may be configured with cooling added to the top part and die used to cut the TIM. A die may be added to the top plate in some exemplary embodiments. Advantageously, a stamping machine (hot and cold) may be able to tamp, cut, and apply TIMs to lids as disclosed herein with only little or no modifications being needed to the stamping machine.

The roll or supply 128 may be provided in various sizing, such as 0.5 inches (12.7 millimeters (mm)), 1 inch (25.4 mm), etc. The roll width may be selected based on the part size. For example, a roll having a width of 0.5 inches (12.7 mm) may be used if the lid 124 (broadly, part) is 10 mm×5 mm. The roll 128 is placed onto an unwind and threaded through the application machine or system 100. If the roll 128 includes a lower liner, the lower liner may be removed as the material advances with small rewind. The lids 124 and die 108 may be oriented in the application machine or system 100 to maximize usage of the thermal interface material. The lids 124 may be placed in a jig for application step to ensure good or perfect positioning and TIM placement. For low volumes, the orientation may be performed manually by hand although for high volumes the orientation may be performed automatically, e.g., by an automated table (e.g., turntable or other, etc.). The system 100 may include a sensor system to advance the rolled TIM material for the next TIM application. Alternatively, the system 100 may be configured with a set distance advance process. Heat and cooling may be provided to improve application robustness.

Exemplary embodiments are disclosed of systems for applying thermal interface material to components. For example, the thermal interface material may be applied to a wide range of substrates and components, such as lids or integrated heat spreaders of integrated circuit (IC) packages, board level shields, heat sources (e.g., a central processing unit (CPU), etc.), heat removal/dissipation structures or components (e.g., a heat spreader, a heat sink, a heat pipe, a vapor chamber, a device exterior case or housing, etc.), etc.

In an exemplary embodiment, the system generally may include a supply of thermal interface material and a die. The die may be operable for tamping and cutting the supply of thermal interface material underneath the die, such that a portion of thermal interface material is tamped and cut from the supply and applied to a corresponding one of the components underneath the die.

The thermal interface material may comprise a non-metal thermal interface material. The portion of thermal interface material may be coupled to the corresponding one of the components without any diffusion bonding or welded joints therebetween.

A liner may be along the thermal interface material. The die may be operable for cutting the portion of thermal interface material through the liner without puncturing the liner to make the cut.

The die may comprise a rounded knife die with a foam filled core. The foam filled core may be usable for tamping the portion of thermal interface material downward onto the corresponding one of the components located underneath the die. The rounded knife die may be usable to cut the portion of thermal interface material.

The system may be configured such the portion of thermal interface material remains on the corresponding one of the components and the liner may be removed from the portion of thermal interface material when the die is removed and raised upwardly away from the portion of thermal interface material. The system may be configured such that the portion of thermal interface material remains on the corresponding one of the components when the die is removed and a next portion of the supply of thermal interface material and a next component is moved into place underneath the die.

The system may comprise a sensor system to advance the supply of thermal interface material for the next application to a subsequent component. Or, the system may be configured with a set distance advance process for the supply of thermal interface material.

The system may include jigs in which the components are placed and oriented relative to the die for placement of the thermal interface material onto the components. The components may comprise lids or integrated heat spreaders of integrated circuit (IC) packages, board level shields, heat sources (e.g., a central processing unit (CPU), etc.), heat removal/dissipation structures or components (e.g., a heat spreader, a heat sink, a heat pipe, a vapor chamber, a device exterior case or housing, etc.), etc.

The system may be configured with heating and/or cooling features for applying heat and/or cooling during the tamping and cutting.

The system may include a roll of the supply of thermal interface material. Rollers may be provided for causing the supply of thermal interface material to unroll from the roll and travel to a location underneath the die. A salvage roll may be used for collecting an unused portion of the supply of thermal interface material that remains after the die has tamped, cut, and applied the thermal interface material to the components. The thermal interface material may be thermal phase change material without any tabs.

Exemplary embodiments are also disclosed of methods of applying thermal interface material to components. For example, the thermal interface material may be applied to a wide range of substrates and components, such as lids or integrated heat spreaders of integrated circuit (IC) packages, board level shields, heat sources (e.g., a central processing unit (CPU), etc.), heat removal/dissipation structures or components (e.g., a heat spreader, a heat sink, a heat pipe, a vapor chamber, a device exterior case or housing, etc.), etc.

In an exemplary embodiment, a method generally includes tamping and cutting a supply of thermal interface material such that a portion of thermal interface material tamped and cut from the supply may be applied to a corresponding one of the components without diffusion bonding of the portion of thermal interface material to the corresponding one of the components.

The tamping and cutting may comprise pressing a die downwardly through a liner disposed along an upper surface of the supply of thermal interface material with pressure, dwell, heating, and cooling.

The tamping and cutting may comprise pressing a die downwardly through a liner disposed along an upper surface of the supply of thermal interface material such that the portion of thermal interface material remains on the corresponding one of the components and the liner may be removed from the portion of thermal interface material when the die may be removed and raised upwardly away from the portion of thermal interface material.

The method may include using the die to cut the portion of thermal interface material through the liner without puncturing the liner.

The die may comprise a rounded knife die with a foam filled core. The method may include using the foam filled core for tamping the portion of thermal interface material downward onto the corresponding one of the components located underneath the die; and using the rounded knife die to cut the portion of thermal interface material from the supply of thermal interface material.

The method may include advancing the corresponding one of the components having the portion of thermal interface material thereon out from under the die; and advancing the supply of thermal interface material and a next component into place under the die. Advancing the supply of thermal interface material into place under the die may comprise using rollers to cause the supply of thermal interface material to unroll from a supply roll and travel to a location underneath the die; and collecting an unused portion of the supply of thermal interface material that remains after the tamping and cutting onto a salvage roll.

The thermal interface material may comprise a non-metal thermal interface material. The method may include coupling the portion of thermal interface material to the corresponding one of the components without any diffusion bonding or welded joints therebetween.

The method may include advancing the supply of thermal interface material for a next application to a component while using a sensor system or a set distance advance process. The method may further comprise placing the components in jigs such that the components are oriented for placement of the thermal interface material onto the components. The components may comprise lids or integrated heat spreaders of integrated circuit (IC) packages, board level shields, heat sources (e.g., a central processing unit (CPU), etc.), heat removal/dissipation structures or components (e.g., a heat spreader, a heat sink, a heat pipe, a vapor chamber, a device exterior case or housing, etc.), etc.

The method may further comprise heating and/or cooling during the tamping and cutting. The thermal interface material may be thermal phase change material without any tabs.

Another exemplary embodiment includes an integrated heat spreader and a thermal interface material tamped, cut, and applied thereon by a system or method disclosed herein. An electronic device may include the integrated heat spreader of claim and central processing unit or processor die. The integrated heat spreader may be operable for spreading heat generated by operation of the central processing unit or processor die.

Another exemplary embodiment includes a board level shield (BLS) and a thermal interface material tamped, cut, and applied thereon by a system or method disclosed herein. The BLS may be suitable for use in providing electromagnetic interference (EMI) shielding for at least one component on a substrate. The BLS may comprise one or more sidewalls defining an opening and configured for installation to the substrate generally about the at least one component on the substrate, and a lid configured to cover the opening defined by the one or more sidewalls. The thermal interface material may be applied to the lid. When the one or more sidewalls are installed to the substrate generally about the at least one component and the lid is covering the opening defined by the one or more sidewalls, the thermal interface material and the lid may cooperate to define a thermally-conductive heat path from the at least one component, and the BLS may be operable for providing EMI shielding for the at least one component. The lid may be integral with or removably attachable to the one or more sidewalls.

Another exemplary embodiment includes an assembly comprising a heat removal/dissipation structure, a printed circuit board having a heat source, and a board level shield having a thermal interface material tamped, cut, and applied thereon by a system or method disclosed herein. The one or more sidewalls are installed to the printed circuit board with the opening over the at least one component. The lid is positioned on the one or more sidewalls such that the opening defined by the one or more sidewalls is covered by the lid. The thermal interface material and the lid cooperate to define a thermally-conductive heat path from the heat source to the heat removal/dissipation structure. The board level shield is operable for providing EMI shielding for the heat source. The heat removal/dissipation structure may be a heat spreader. The heat source may be an integrated circuit on the printed circuit board.

A wide range of thermal interface materials may be used in exemplary embodiments for the thermal interface material 120 shown in FIG. 2. Advantageously, exemplary embodiments disclosed herein may allow a TIM to be made that will have relaxed properties over current TIMs. Ease of handling and application are important for TIMs, although softness, shear thinning, and modulus that help performance result in more difficult to apply materials. The exemplary application processes disclosed herein may allow materials that are typically hard to apply but have better performance to be applied easier.

Example thermal interface materials that may be used in exemplary embodiments include thermal gap fillers, thermal phase change materials, thermally-conductive EMI absorbers or hybrid thermal/EMI absorbers, thermal putties, thermal pads, etc. For example, exemplary embodiments may include a thermally-conductive EMI absorbers or hybrid thermal/EMI absorbers tamped, cut, and applied to a portion of an EMI shield, such as a cover or lid of a board level shield.

Example embodiments may include one or more thermal interface materials of Laird, such as any one or more of the Tputty™ 502 series thermal gap fillers, Tflex™ series gap fillers (e.g., Tflex™ 300 series thermal gap filler materials, Tflex™ 600 series thermal gap filler materials, Tflex™ 700 series thermal gap filler materials, etc.), Tpcm™ series thermal phase change materials (e.g., Tpcm™ 580 series phase change materials, Tpcm™ 780 series phase change materials, Tpcm™ 900 series phase change materials etc.), Tpli™ series gap fillers (e.g., Tpli™ 200 series gap fillers, etc.), IceKap™ series thermal interface materials, and/or CoolZorb™ series thermally conductive microwave absorber materials (e.g., CoolZorb™ 400 series thermally conductive microwave absorber materials, CoolZorb™ 500 series thermally conductive microwave absorber materials, CoolZorb™ 600 series thermally conductive microwave absorber materials, etc.), etc. In some exemplary embodiments, the thermal interface material may comprise a compliant gap filler having high thermal conductivity. By way of example, the thermal interface material may comprise a thermal interface material of Laird, such as one or more of Tflex™ 200, Tflex™ HR200, Tflex™ 300, Tflex™ 300TG, Tflex™ HR400, Tflex™ 500, Tflex™ 600, Tflex™ HR600, Tflex™ SF600, Tflex™ 700, Tflex™ SF800 thermal gap fillers.

The thermal interface materials disclosed herein may comprise an elastomer and/or ceramic particles, metal particles, ferrite EMPRFI absorbing particles, metal or fiberglass meshes in a base of rubber, gel, or wax, etc. The thermal interface materials may include compliant or conformable silicone pads, non-silicone based materials (e.g., non-silicone based gap filler materials, thermoplastic and/or thermoset polymeric, elastomeric materials, etc.), silk screened materials, polyurethane foams or gels, thermally-conductive additives, etc. The thermal interface materials may be configured to have sufficient conformability, compliability, and/or softness (e.g., without having to undergo a phase change or reflow, etc.) to adjust for tolerance or gaps by deflecting at low temperatures (e.g., room temperature of 20° C. to 25° C., etc.) and/or to allow the thermal interface materials to closely conform (e.g., in a relatively close fitting and encapsulating manner, etc.) to a mating surface when placed in contact with (e.g., compressed against, etc.) the mating surface, including a non-flat, curved, or uneven mating surface.

The thermal interface materials disclosed herein may include a soft thermal interface material formed from elastomer and at least one thermally-conductive metal, boron nitride, and/or ceramic filler, such that the soft thermal interface material is conformable even without undergoing a phase change or reflow. In some exemplary embodiments, the first and/or second thermal interface materials may include ceramic filled silicone elastomer, boron nitride filled silicone elastomer, or a thermal phase change material that includes a generally non-reinforced film.

Exemplary embodiments may include one or more thermal interface materials having a high thermal conductivity (e.g., 1 W/mK (watts per meter per Kelvin), 1.1 W/mK, 1.2 W/mK, 2.8 W/mK, 3 W/mK, 3.1 W/mK, 3.8 W/mK, 4 W/mK, 4.7 W/mK, 5 W/mK, 5.4 W/mK, 6 W/mK, etc.) depending on the particular materials used to make the thermal interface material and loading percentage of the thermally conductive filler, if any. These thermal conductivities are only examples as other embodiments may include a thermal interface material with a thermal conductivity higher than 6 W/mK, less than 1 W/mK, or other values between 1 and 6 W/mk. Accordingly, aspects of the present disclosure should not be limited to use with any particular thermal interface material as exemplary embodiments may include a wide range of thermal interface materials.

A wide range of materials may be used in exemplary embodiments disclosed herein for the lids (broadly, parts) including electrically-conductive materials, such as metals (e.g., aluminum, copper, etc.), alloys, natural graphite, synthetic graphite, or other suitable materials, etc. By way of example, a non-exhaustive list of exemplary materials from which the EMI shield or portion thereof may be made include cold rolled steel, nickel-silver alloys, copper-nickel alloys, stainless steel, tin-plated cold rolled steel, tin-plated copper alloys, carbon steel, brass, copper, aluminum, copper-beryllium alloys, phosphor bronze, steel, alloys thereof, a plastic material coated with electrically-conductive material, or any other suitable electrically-conductive and/or magnetic materials. The materials disclosed in this application are provided herein for purposes of illustration only as different materials may be used depending, for example, on the particular application.

In addition, the thermal interface materials may be tamped, cut, and applied to a wide range of parts or components, including lids or integrated heat spreaders of integrated circuit (IC) packages, board level shields (e.g., a removable lid or cover of a board level shield (BLS), etc.), heat sources (e.g., a central processing unit (CPU), etc.), heat removal/dissipation structures or components (e.g., a heat spreader, a heat sink, a heat pipe, a vapor chamber, a device exterior case or housing, etc.), etc. Accordingly, aspects of the present disclosure should not be limited to use with any single type of part or component or limited to application to any specific location or portion of a part or component.

In exemplary embodiments, a thermal interface material may be tamped, cut, and applied to a lid or cover of a board level shield (BLS). The BLS lid or cover may be integral with or removably attachable to sidewalls of the BLS. For example, the BLS may include sidewalls that are integrally formed with the upper surface, cover, lid, or top of the BLS. For example, the sidewalls and upper surface may be formed by stamping the same electrically-conductive piece of material and then folding the stamped material such that the sidewalls are generally perpendicular to the upper surface. Alternatively, the sidewalls may be made separately and not integrally formed with the upper surface of the BLS. In some exemplary embodiments, the BLS may comprise a two-piece shield in which the upper surface, cover, lid, or top is removable from and reattachable to the sidewalls. In some exemplary embodiments, the BLS may include one or more interior walls, dividers, or partitions that are attached to and/or integrally formed with the BLS. In such exemplary embodiments, the BLS cover, sidewalls, and interior walls may cooperatively define a plurality of individual EMI shielding compartments.

In some exemplary embodiments, multiple different thermal interface materials may be tamped, cut, and applied to either or both sides of the lids 124. For example, multiple different thermal interface materials may be tamped, cut, and applied along the lower or inner side of a BLS lid or cover, which have different thicknesses to accommodate for varying heights of the devices, components, etc., that will be under the BLS. The multiple different thermal interface materials along the upper or outer side of the lid may also have different thicknesses to accommodate for varying thicknesses of the heat spreader or other heat removal/dissipation structures.

Example embodiments disclosed herein may be used with a wide range of heat sources, electronic devices, and/or heat removal/dissipation structures or components (e.g., a heat spreader, a heat sink, a heat pipe, a device exterior case or housing, etc.). For example, a heat source may comprise one or more heat generating components or devices (e.g., a CPU, die within underfill, semiconductor device, flip chip device, graphics processing unit (GPU), digital signal processor (DSP), multiprocessor system, integrated circuit, multi-core processor, etc.). Generally, a heat source may comprise any component or device that has a higher temperature than the thermal interface material or otherwise provides or transfers heat to the thermal interface material regardless of whether the heat is generated by the heat source or merely transferred through or via the heat source. Accordingly, aspects of the present disclosure should not be limited to any particular use with any single type of heat source, electronic device, heat removal/dissipation structure, etc.

Exemplary embodiments may provide one or more (but not necessarily any or all) of the following features or advantages, such as the elimination of tabs and reduced costs as compared to some conventional phase change material (PCM) application processes having tabbed parts that add high cost. Exemplary embodiments may help solve problems such as issues that customers have in applying tabbed parts correctly, issues with liner release, limitations on part configuration, shape and size, difficulty in a keeping material clean during additional steps after forming in a clean room, and/or shipping tabbed parts without distortion. Exemplary embodiments disclosed herein may allow a standard material (e.g., standard width, thickness, and/or length, etc.) to be provided, which may then be used with different dies that can be changed as needed for various shapes and sizes. Exemplary embodiments disclosed herein may provide a relatively simple forming design from pot to finished rolls, may provide a compact process and smaller clean room requirements (Type 2), may only require limited work-in-progress (WIP) dollars, may allow for a relatively simple/smaller part numbers list, thickness of PCM and width, may allow for a wide variety of die shapes and parts (e.g., FIG. 3, etc.) that are not feasible in tabbed format cost effectively, may allow the smallest size providable to become a non-issue (e.g., FIG. 3, etc.), may allow liner release variance issues to be less of an issue, and/or may allow extrusion screened "clean" material to stay between liners until applied to lid. In some exemplary embodiments, the TIM may be applied quickly and without distortion or trapped air, and the parts may be clean without pump out.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. In addition, advantages and improvements that may be achieved with one or more exemplary embodiments of the present disclosure are provided for purpose of illustration only and do not limit the scope of the present disclosure, as exemplary embodiments disclosed herein may provide all or none of the above mentioned advantages and improvements and still fall within the scope of the present disclosure.

Specific dimensions, specific materials, and/or specific shapes disclosed herein are example in nature and do not limit the scope of the present disclosure. The disclosure herein of particular values and particular ranges of values for given parameters are not exclusive of other values and ranges of values that may be useful in one or more of the examples disclosed herein. Moreover, it is envisioned that any two particular values for a specific parameter stated herein may define the endpoints of a range of values that may be suitable for the given parameter (i.e., the disclosure of a first value and a second value for a given parameter can be interpreted as disclosing that any value between the first and second values could also be employed for the given parameter). For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The term "about" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. For example, the terms "generally", "about", and "substantially" may be used herein to mean within manufacturing tolerances. Or for example, the term "about" as used herein when modifying a quantity of an ingredient or reactant of the invention or employed refers to variation in the numerical quantity that can happen through typical measuring and handling procedures used, for example, when making concentrates or solutions in the real world through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the disclosure. Individual elements, intended or stated uses, or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for applying thermal interface materials to components, the system comprising:
   a supply of thermal interface material having a high thermal conductivity; and
   a die operable for both tamping and cutting a portion of the thermal interface material from the supply that is between the die and a corresponding one of the components, whereby the portion of the thermal interface material is removed from the supply and applied as a conformable thermal pad to the corresponding one of the components without diffusion bonding of the portion of the thermal interface material to the corresponding one of the components, without welded joints between the portion of the thermal interface material and the corresponding one of the components, and without trapped air within the conformable thermal pad.

2. The system of claim 1, wherein the supply of thermal interface material comprises a supply of non-metal thermal interface material having a thermal conductivity of at least 1 Watt per meter per Kelvin, and wherein a portion of the non-metal thermal interface material is applied as the conformable thermal pad to the corresponding one of the components without adhesive between the portion of the non-metal thermal interface material and the corresponding one of the components.

3. The system of claim 1, wherein:
   the supply of thermal interface material further includes a liner along a surface of the thermal interface material; and
   the die is movable downwardly through the liner such that the downward movement of the die through the liner also moves and applies the portion of the thermal interface material from the liner downwardly onto the corresponding one of the components without cutting or transferring the liner from the supply and reduces a thickness of the portion of the thermal interface material.

4. The system of claim 3, wherein the die is operable for pushing the liner downwardly through the portion of the thermal interface material for downwardly severing the portion of the thermal interface material from the supply without cutting the liner and thereby transferring the portion of the thermal interface material from the liner onto the corresponding one of the components without having to puncture the liner, and wherein the die is operable for forcing the liner down into the portion of the thermal interface material such that the thickness of the portion of the thermal interface material is reduced or pushed out of the way, thereby providing the portion of the thermal interface material with tapered edges in a thickness dimension along all sides of the portion of the thermal interface material that has been transferred to the corresponding one of the components.

5. The system of claim 3, wherein the system is configured such that the portion of the thermal interface material remains on the corresponding one of the components and such that a corresponding portion of the liner is automatically removed by the die from the portion of the thermal interface material transferred onto the corresponding one of the components and remains with an unused salvage portion of the supply when the die is removed and moved relatively away from the portion of the thermal interface material.

6. The system of claim 1, wherein the system comprises a sensor system to advance the supply of thermal interface material for a next application of another portion of the thermal interface material to a subsequent component of the components after the system has applied the portion of the thermal interface material to the corresponding one of the components.

7. The system of claim 1, wherein the system includes the components that comprise:
   integrated heat spreaders of integrated circuit packages comprising thermally-conductive metal lids configured to rest on top of central processing units or processor dies; or
   lids of board level shields including sidewalls, the lids being integral with or removably attachable to the sidewalls of the board level shields, whereby each said board level shield is configured such that when the sidewalls are installed to a substrate about at least one component and the lid is covering an opening defined by the sidewalls, the portion of the thermal interface material applied to the lid cooperates with the lid to define a thermally-conductive heat path from the at least one component and the board level shield is operable for providing electromagnetic interference (EMI) shielding for the at least one component.

8. The system of claim 1, wherein the supply of thermal interface material is a supply of thermal phase change material having a thermal conductivity of at least 1 Watt per meter per Kelvin, and wherein the system includes the components that comprise lids of board level shields including sidewalls, the lids being integral with or removably attachable to the sidewalls of the board level shields, whereby each said board level shield is configured such that when the sidewalls are installed to a substrate about at least one component and the lid is covering an opening defined by the sidewalls, a portion of the thermal phase change material applied to the lid cooperates with the lid to define a thermally-conductive heat path from the at least one component and the board level shield is operable for providing electromagnetic interference (EMI) shielding for the at least one component.

9. The system of claim 1, wherein the system is configured to be operable for applying multiple different thermal interface materials to either one or both sides of the components.

10. The system of claim 1, wherein the system comprises jigs in which the components are placed and oriented relative to the die for placement of the thermal interface material onto the components, and wherein the die comprises a knife die operable for cutting the portion of the thermal interface material from the supply and a foam filled core usable for tamping the portion of the thermal interface material onto the corresponding one of the components.

11. The system of claim 10, wherein the system comprises a sensor system to advance the supply of thermal interface material for a next application of another portion of the thermal interface material to a subsequent component of the components after the system has applied the portion of the thermal interface material to the corresponding one of the components.

12. The system of claim 10, wherein the system is configured with a set distance advance process for the supply of thermal interface material.

13. The system of claim 1, wherein the system includes active cooling features added to the die for active cooling of the portion of the thermal interface material as the die pushes against and removes the portion of the thermal interface material during application of the portion of the thermal interface material to the corresponding one of the components.

14. The system of claim 1, wherein the die comprises a foam filled core usable for tamping the portion of the thermal interface material onto the corresponding one of the components, and wherein the system further comprises:
a roll including the supply of thermal interface material;
rollers for causing the supply of thermal interface material to unroll from the roll and travel to a location aligned with the die; and
a salvage for collecting an unused portion of the supply of thermal interface material that remains after the thermal interface material has been applied to the components.

15. The system of claim 1, wherein:
the die is operable for tamping and cutting the portion of the thermal interface material from the supply that is between the die and the corresponding one of the components; and
the system is configured to be operable for applying multiple different thermal interface materials to either one or both sides of the components.

16. The system of claim 1, wherein the die is operable for both downwardly tamping and downwardly cutting the portion of the thermal interface material from the supply that is between the die and the corresponding one of the components, whereby a thickness of the portion of the thermal interface material is reduced or pushed out of the way thereby providing the portion of the thermal interface material with tapered edges in a thickness dimension along all four sides of the portion of the thermal interface material that has been transferred to the corresponding one of the components.

17. The system of claim 1, wherein:
the supply of thermal interface material comprises a supply of thermal interface material along a liner wherein the thermal interface is naturally tacky and has a thermal conductivity of at least 1 Watt per meter per Kelvin; and
the die is operable for transferring the portion of the thermal interface material from the liner onto the corresponding one of the components without transferring the liner from the supply, whereby the portion of the thermal interface material self-adheres to the corresponding one of the components without any additional adhesive between the portion of the thermal interface material and the corresponding one of the components.

18. The system of claim 1, wherein:
the supply of thermal interface material comprises a supply of thermal interface material along a liner; and
the die is operable for transferring the portion of the thermal interface material from the liner onto the corresponding one of the components without transferring, from the supply, a corresponding portion of the liner from which the portion of the thermal interface material was transferred whereby the corresponding portion of the liner remains with an unused salvage portion of the supply.

19. The system of claim 1, wherein:
the supply of thermal interface material comprises a supply of thermal interface having an initial thickness along a liner; and
the die is operable for forcing the liner down into the portion of the thermal interface material such that the portion of the thermal interface material has a thickness less than the initial thickness.

20. The system of claim 1, wherein the system is configured such that the components are spaced apart by a greater distance than which the supply of thermal interface material is advanced for a next application of another portion of the thermal interface material to a subsequent component of the components after the system has applied the portion of the thermal interface material to the corresponding one of the components.

21. The system of claim 1, wherein:
the supply of thermal interface material comprises a supply of thermal interface material along a liner having a width; and
the die comprises a knife die operable for cutting the portion of the thermal interface material from the supply, whereby the die is operable for transferring the portion of the thermal interface material from the liner onto the corresponding one of the components such that the portion of the thermal interface material has a width about equal to the width of the thermal interface material along the liner.

22. The system of claim 1, wherein the supply of thermal interface material comprises a supply of thermal phase change material along a liner and that has a thermal conductivity of at least 1 Watt per meter per Kelvin.

23. The system of claim 1, wherein the supply of thermal interface material comprises a supply of thermal interface material along a liner and that is naturally tacky, self-adherable to the components without additional adhesive, and has a thermal conductivity of at least 1 Watt per meter per Kelvin.

24. The system of claim 1, wherein the system is configured such that the die is operable for pushing against and removing the portion of the thermal interface material from the supply with pressure, dwell, heating, and cooling.

25. The system of claim 1, wherein:
the supply of thermal interface material comprises a supply of thermal interface material along a liner; and
the system is configured such that the die is operable for transferring the portion of the thermal interface material from the liner onto the corresponding one of the components with pressure, dwell, heating, and cooling.

26. A system for individually applying thermal interface materials to individual ones of a plurality of components, the system comprising:
a supply of thermal interface material along a liner; and a die operable for transferring a portion of the thermal interface material from the liner onto a corresponding one of the components without cutting or transferring the liner from the supply;

wherein:

the die comprises a rounded knife die having a foam filled core;

the foam filled core is usable for tamping the portion of the thermal interface material onto the corresponding one of the components;

the rounded knife die is usable to cut the portion of the thermal interface material from the supply through the liner; and the system is configured such that when the die is moved relatively away from the corresponding one of the components:

the portion of the thermal interface material remains on the corresponding one of the components; and a corresponding portion of the liner is automatically removed by the die from the portion of the thermal interface material transferred onto the corresponding one of the components and remains with an unused salvage portion of the supply.

27. The system of claim 26, wherein the system comprises a sensor system to advance the supply of thermal interface material for a next application of another portion of the thermal interface material to a subsequent component of the components after the system has applied the portion of the thermal interface material to the corresponding one of the components.

28. The system of claim 26, wherein the system includes active cooling features added to the die for active cooling of the portion of the thermal interface material as the die tamps and cuts the portion of the thermal interface material during application of the portion of the thermal interface material to the corresponding one of the components, and wherein the die is operable for forcing the liner down into the portion of the thermal interface material such that a thickness of the portion of the thermal interface material is reduced or pushed out of the way, thereby providing the portion of the thermal interface material with tapered edges in a thickness dimension of the portion of the thermal interface material that has been transferred to the corresponding one of the components.

29. The system of claim 26, wherein the supply of thermal interface material comprises a supply of thermal interface material having a thermal conductivity of at least 1 Watt per meter per Kelvin, and wherein the system includes the components that comprise lids of board level shields including sidewalls, the lids being integral with or removably attachable to the sidewalls of the board level shields, whereby each said board level shield is configured such that when the sidewalls are installed to a substrate about at least one component and the lid is covering an opening defined by the sidewalls, the portion of the thermal interface material applied to the lid cooperates with the lid to define a thermally-conductive heat path from the at least one component and the board level shield is operable for providing electromagnetic interference (EMI) shielding for the at least one component.

* * * * *